United States Patent
Chen et al.

(10) Patent No.: US 12,180,519 B2
(45) Date of Patent: Dec. 31, 2024

(54) COCAINE ESTERASE MUTANT AND USE THEREOF

(71) Applicant: Hangzhou Normal University, Hangzhou (CN)

(72) Inventors: Xiabin Chen, Hangzhou (CN); Jianzhuang Yao, Hangzhou (CN); Shurong Hou, Hangzhou (CN); Xingyu Deng, Hangzhou (CN); Yun Zhang, Hangzhou (CN); Junsen Tong, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 0 days.

(21) Appl. No.: 18/489,816

(22) Filed: Oct. 18, 2023

(65) Prior Publication Data
US 2024/0117329 A1    Apr. 11, 2024

Related U.S. Application Data

(63) Continuation of application No. PCT/CN2022/089839, filed on Apr. 28, 2022.

(30) Foreign Application Priority Data

Jul. 5, 2021 (CN) .......................... 202110755649.4

(51) Int. Cl.
| | | |
|---|---|---|
| *C12N 9/18* | (2006.01) | |
| *B09C 1/10* | (2006.01) | |
| *C02F 3/34* | (2023.01) | |
| *C02F 101/38* | (2006.01) | |

(52) U.S. Cl.
CPC ................. *C12N 9/18* (2013.01); *B09C 1/10* (2013.01); *C02F 3/342* (2013.01); *C12Y 301/01084* (2013.01); *C02F 2101/38* (2013.01)

(58) Field of Classification Search
CPC ... C12N 9/18; B09C 1/10; C02F 3/342; C02F 2101/38; C12Y 301/01084
USPC ......................................................... 435/197
See application file for complete search history.

(56) References Cited

U.S. PATENT DOCUMENTS

| | | |
|---|---|---|
| 2013/0039900 A1 | 2/2013 | Sunahara et al. |
| 2016/0122732 A1 | 5/2016 | Zhan et al. |

FOREIGN PATENT DOCUMENTS

| | | |
|---|---|---|
| AU | 2007272955 A1 | 1/2008 |
| CN | 101583374 A | 11/2009 |
| CN | 101903038 A | 12/2010 |
| WO | 2008008358 A2 | 1/2008 |

OTHER PUBLICATIONS

Internation Search Report of PCT/CN2022/089839, Mailed Aug. 1, 2022.

Huang, X. et al., "Cocaine esterase-cocaine binding process and the free energy profiles by molecular dynamics andpotential of mean force simulations", Journal of Physical Chemistry B, vol. 116, No. 10, Mar. 15, 2012, pp. 3361-3368, see entire document.

*Primary Examiner* — Jennifer M. H. Tichy

(57) ABSTRACT

Disclosed are a cocaine esterase mutant and use thereof. The cocaine esterase mutant is obtained by mutating a wildtype cocaine esterase, an amino acid sequence of the wildtype cocaine esterase is shown as SEQ ID No. 1, the cocaine esterase mutant is T172R/G173Q/L196C/I301C, or additionally added with V116K point mutation, or additionally added with A51 site mutation, and the A51 site mutation is L, Y, V, F or W. Catalytic efficiency of the cocaine esterase mutant screened on a cocaine toxic metabolite benzoylecgonine is greatly improved compared with that of a wildtype enzyme.

4 Claims, 2 Drawing Sheets

Specification includes a Sequence Listing.

COCAINE ESTERASE MUTANT AND USE THEREOF

CROSS-REFERENCE TO RELATED APPLICATIONS

This application is a continuation of International Patent Application No. PCT/CN2022/089839 with a filing date of Apr. 28, 2022, designating the United States, and further claims priority to Chinese Patent Application No. 202110755649.4 with a filing date of Jul. 5, 2021. The content of the aforementioned applications, including any intervening amendments thereto, are incorporated herein by reference.

SEQUENCE LISTING

The present application contains a sequence listing which was filed electrically in XML format and is hereby incorporated by reference in its entirety. The XML-format sequence listing file was created on Jul. 1, 2024, named as "SEQUENCE LISTING", and is 33kb in size.

TECHNICAL FIELD

The present invention relates to the technical field of biomedicine, in particular to a cocaine esterase mutant and use thereof.

BACKGROUND

Cocaine abuse and addiction is a serious medical and social problem in modern society. So far, no drug has been approved for cocaine detoxification treatment. The disastrous medical and social consequences of cocaine abuse make the development of anti-cocaine drugs a top priority. In vivo, about 40% of cocaine is rapidly bio-converted by butyrylcholinesterase (BChE) and carboxyesterase-2 (CE-2) to inactive metabolite ecgonine methyl ester (EME), while 45% of cocaine is hydrolyzed by carboxyesterase-1 (CE-1) in liver to toxic metabolite benzoyllecgonine (BZE) (FIG. 1). BZE has similar physiological activity to cocaine, and BZE is considered to be the main contributor to the long-term toxicity of cocaine due to its long half-life in vivo. In addition, BZE is one of the main residual pollutants of addictive drugs in the environment, which has an important impact on the ecosystem.

The ideal treatment of cocaine abuse requires not only the rapid elimination of the toxicity of cocaine, but also the elimination of the toxicity of the toxic metabolite BZE of cocaine. Based on the research strategy of combining computer aided design with enzyme engineering, scientists have designed and developed a series of highly efficient and heat-stable cocaine metabolizing enzymes, including human butyrylcholinesterase (BChE) mutants and bacterial cocaine esterase (CocE) mutants, which can effectively eliminate the toxicity of cocaine (Larsen N A, Turner J M, Stevens J, Rosser S J, Basran A, Lerner R A, Bruce N C, Wilson I A. Crystal structure of a bacterial cocaine esterase, Nat Struct Biol 2002, 9 (1): 17-21). On this basis, further degradation of BZE is the key to complete detoxification of cocaine, so it is of great significance to develop efficient metabolizing enzymes for BZE degradation for complete detoxification of cocaine.

Endogenous BChE is the only one that can hydrolyze BZE into non-toxic ecgonine (ECG) and benzoic acid. However, due to the high glycosylation of natural BChE, efficient and economical recombinant expression of BChE has always been a difficult problem in the industry, which is difficult in later development. Therefore, it is of great application value to find BZE metabolizing enzymes with economic expression and high catalytic activity.

CocE may be economically and efficiently expressed by a prokaryotic cell expression system, and the recombinant protein has good safety in human (the CocE T172R/G173Q mutant has completed the clinical test II phase of cocaine detoxification, and proved that the mutant is safe and effective). Nasser, A. F., et al. J. Addit. Dis. 2014, 33, 289-302). Therefore, CocE is a very ideal candidate BZE metabolizing enzyme. However, the catalytic efficiency of natural CocE to BZE is too low, and a great improvement is needed to meet the requirement of efficiently removing the toxicity of BZE.

SUMMARY

The present invention aims to design and obtain a brand-new high-activity CocE mutant to further improve the catalytic activity of a cocaine toxic metabolite BE, may be used for clinical treatment of cocaine intoxication, and meet the clinical use requirement.

Based on the catalytic mechanism of phenyl ester hydrolysis by esterase and the classical catalytic triad structure of esterase, we found cocaine esterase as a candidate enzyme for hydrolyzing BZE by searching through Rosetta software. We found for the first time that CocE could catalyze BZE hydrolysis to give ecgonine and benzoic acid, with BZE catalytic parameters as follows: $k_{cat}=301.2$ min$^{-1}$, and $K_M=5153$ μM.

A cocaine esterase mutant is obtained by mutating a wildtype cocaine esterase, wherein an amino acid sequence of the wildtype cocaine esterase is shown as SEQ ID No. 1, and the cocaine esterase mutant is one of the following:
(1) V116K,
(2) T172R/G173Q/V116K,
(3) T172R/G173Q/L196C/I301C/V116K,
(4) T172R/G173Q/L196C/I301C/V116K/A51L,
(5) T172R/G173Q/L196C/I301C/V116K/A51Y,
(6) T172R/G173Q/L196C/I301C/V116K/A51V,
(7) T172R/G173Q/L196C/I301C/V116K/A51F, and
(8) T172R/G173Q/L196C/I301C/V116K/A51W.

The present invention further provides use of the cocaine esterase mutant for preparing a medicament for treating cocaine intoxication.

The present invention further provides use of the cocaine esterase mutant for preparing a hydrolytic agent for hydrolyzing benzoylecgonine into ecgonine and benzoic acid.

The present invention further provides use of the cocaine esterase mutant for treating cocaine or benzoylecgonine contamination in water or soil.

The present invention also provides a medicament for treating cocaine intoxication, wherein an active ingredient is the cocaine esterase mutant.

The medicament further comprises a medically acceptable additive.

The present invention also provides a reagent for treating cocaine or benzoylecgonine contamination in water or soil, wherein an effective ingredient is the cocaine esterase mutant.

The present invention also provides a gene encoding the cocaine esterase mutant.

The present invention also provides an expression vector containing the gene.

The present invention also provides a recombinant expression cell containing the expression vector.

The present invention also provides use of the gene according for treating cocaine or benzoylecgonine contamination in water or soil.

The present invention obtains a series of mutations through computer aided design, and constructs a CocE mutant by adopting a point mutation PCR method; expresses and purifies the recombinant protease; and verifies the enzyme activity by in vitro and in vivo enzymatic reactions, and screens high-activity mutants.

According to the research of the present invention, the catalytic efficiency of the V116K mutant obtained by mutating the $116^{th}$ V (valine) of cocaine esterase into K (lysine) on the cocaine toxic metabolite benzoylecgonine is greatly improved compared with the wildtype enzyme. On the basis of the mutation of V116K, screening is further carried out, and the catalytic efficiency of the screened cocaine esterase mutant on the cocaine toxic metabolite benzoylecgonine is further improved.

BRIEF DESCRIPTION OF THE DRAWINGS

FIG. 3A is a curve of a BEZ concentration in blood over time; and FIG. 3B is a curve of a metabolite BA concentration in blood over time; wherein, 5M-51L represents T172R/G173Q/L196C/I301C/V116K/A51L; and 5M-51V represents T172R/G173Q/L196C/I301C/V116K/A51V.

DETAILED DESCRIPTION

Figure 1:
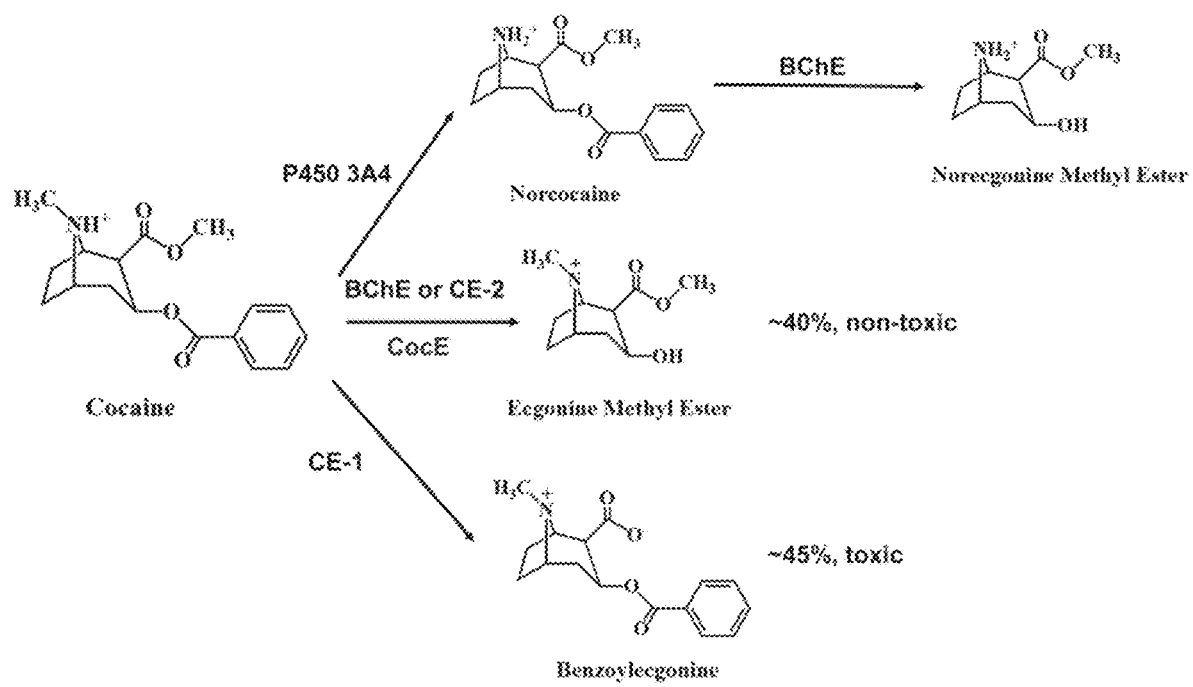
FIG. 1 is a metabolic pathway of cocaine.
Figure 2:
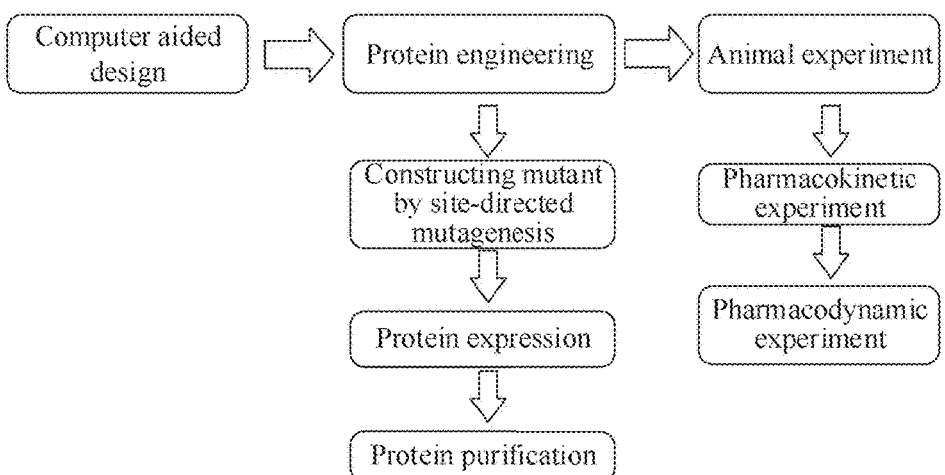
FIG. 2 is a technical roadmap of the present invention.

The overall technical route of the present invention is shown in FIG. 2.

Embodiment 1: Site-Directed Mutagenesis

CocE mutants were obtained by site-directed mutagenesis.

Firstly, cDNA (GenBank #AF173165.1, synthesized by Shanghai Generay Biotech) of wildtype CocE was constructed into an *Escherichia coli* expression vector pET-22b (+) (provided by Shanghai Generay Biotech, and a target gene containing C-terminal-6×His was inserted into NdeI and XhoI restriction site). Wildtype CocE plasmid was used as a template to design mutant primers, PCR products of the mutants were obtained through PCR (KOD One Mater Mix, Shanghai Toyobo) amplification. DNA templates in the products were removed through DpnI (Thermo Scientific, FD1703), and then transformed into competent cells (DH5α) to cyclize the PCR products. The transformed competent cell bacterial solution was coated on LB solid medium containing 100 μg/ml ampicillin, and cultured at 37° C. for 15 hours. Monoclones were selected and the mutant plasmids were extracted by plasmid extraction kit. The mutant plasmids with correct sequence were confirmed by DNA sequencing. For those with multiple mutations, one mutation was followed by next round of mutation. Mutant primer design was shown in table 1.

TABLE 1

Primer sequences used for site-directed mutagenesis

| Mutation site | Primer (5'-3') | |
|---|---|---|
| T172R/ | Forward primer | SEQ ID No. 20 |
| G173Q | Reverse primer | SEQ ID No. 21 |
| L196C | Forward primer | SEQ ID No. 22 |
| | Reverse primer | SEQ ID No. 23 |
| I301C | Forward primer | SEQ ID No. 24 |
| | Reverse primer | SEQ ID No. 25 |
| V116K | Forward primer | SEQ ID No. 26 |
| | Reverse primer | SEQ ID No. 27 |
| A51L | Forward primer | SEQ ID No. 28 |
| | Reverse primer | SEQ ID No. 29 |
| A51Y | Forward primer | SEQ ID No. 30 |
| | Reverse primer | SEQ ID No. 31 |
| A51V | Forward primer | SEQ ID No. 32 |
| | Reverse primer | SEQ ID No. 33 |
| A51F | Forward primer | SEQ ID No. 34 |
| | Reverse primer | SEQ ID No. 35 |
| A51W | Forward primer | SEQ ID No. 36 |
| | Reverse primer | SEQ ID No. 37 |

Embodiment 2: Protein Expression and Purification

The successfully constructed mutant plasmids were transformed into *Escherichia coli* BL21 competent cells to express proteins, the bacterial solution was inoculated into an LB liquid medium (containing 100 μg/ml ampicillin), subjected to enlarge cultivation on a shaker at 37° C. and 250 rpm until $OD_{600}$=0.6-0.8, and then the bacterial solution was cooled to 15° C. IPTG (Sigma, 367-93-1) was added until a final concentration was 1 mM, and then protein expression was induced at 15° C. and 180 rpm for 15 hours. The cells were collected and re-suspended in 50 mM Tris-HCl buffer (pH 7.4) containing 150 mM NaCl. *Escherichia coli* cells were disrupted with a precooled high-pressure cell disrupter (SCIENTZ JG-IA, Ningbo Scientz), centrifuged at 9,000 rpm for 45 minutes and then the supernatant was collected. The supernatant was mixed with a cobalt medium (Takara, TALON Metal Affinity Resin) by rotation at 4° C. for 2 hours to bind the protein containing 6×His to the medium. The binding solution was added into a gravity column, naturally flowing out under the action of gravity, and the target protein was purified by using a gradient elution method of imidazole with different concentrations. The eluted components were collected in a 30K (Millipore) ultrafiltration tube, and the buffer was replaced by centrifugal concentration. The protein was stored in solution S (50 mM HEPES, 20% D-sorbitol, 1 M glycine, pH 7.4). Protein concentration was determined by Bradford kit (Sangon Biotech, C503031-1000).

Embodiment 3: Enzyme Activity Analysis

Firstly, an experimental method for detecting a substrate BZE and a product benzoic acid BA by HPLC was established. Both BZE and BA had strong ultraviolet absorption at 230 nm. In HPLC analysis, acetonitrile and 0.1% formic acid were used as mobile phases to separate BZE and BA by C18 liquid chromatography column. The absorption of BZE and BA at wavelength 230 nm was detected by an ultraviolet detector, and linear standard curves of BZE and BA were obtained. The activity of BZE reaction catalyzed by CocE was determined, and the reaction temperature was 25° C., with three repetitions in each group. An enzymatic reaction was started by 50 μL of substrate BZE solution with 50 μL of enzyme solution (diluted with 0.1 M phosphate buffer (pH 7.4)). The specific reaction conditions were shown in Table 2.

TABLE 2

Conditions for in vitro catalytic reaction of high-activity mutant enzyme to substrate BZE

| Enzyme and concentration thereof | BZE concentration(μM) | Reaction time (min) |
|---|---|---|
| Wildtype, T172R/G173Q, T172R/G173Q/L196C/I301C, (50 nM) | 100, 250 500, 1,000, 2,500, 5,000, 7,500, 12,500 | 4 10 |
| T172R/G173Q/L196C/I301C/V116K, T172R/G173Q/L196C/I301C/V116K/A51L, T172R/G173Q/L196C/I301C/V116K/A51Y, (4 nM) | 5, 10, 20, 50, 100, 200 500, 1,000 | 2 5 |
| V116K, T172R/G173Q/V116K, T172R/G173Q/L196C/I301C/V116K/A51V, T172R/G173Q/L196C/I301C/V116K/A51F, T172R/G173Q/L196C/I301C/V116K/A51W, (4 nM) | 5, 10, 20, 50, 100, 200 500, 1,000 | 4 10 |

50 μL of 10% perchloric acid was added to stop the reaction, and then, 50 μL of acetonitrile was added, and the mixture was centrifuged at 12,000 rpm for 5 minutes. Then, the supernatant was diluted to an appropriate multiple and injected into 100 L. The peak time, peak areas and curves of BZE and BA were compared, and the residual BZE concentration and the BA concentration in the reaction sample were calculated. The $k_{cat}$ and $K_M$ of each mutant could be obtained by calculating the reaction rates of BA catalyzed by enzyme at different substrate concentrations, drawing a kinetic curve of the enzyme reaction with GraphPad Prism 8, and performing Michaelis-Menten kinetic analysis. The results were shown in Table 3.

TABLE 3

Catalytic kinetic parameters of high-activity mutant enzyme to substrate BZE

| Mutation site | $K_M$ (μM) | $k_{cat}$ (min$^{-1}$) | $K_{eff}$ (M$^{-1}$min$^{-1}$) | RCE |
|---|---|---|---|---|
| Wildtype WT | 5,153 | 301.2 | $5.85 \times 10^4$ | 1.0 |
| V116K | 89.57 | 320.4 | $3.58 \times 10^6$ | 61.2 |
| T172R/G173Q | 4,355 | 418.7 | $9.61 \times 10^4$ | 1.6 |
| T172R/G173Q/V116K | 65.63 | 425.2 | $6.48 \times 10^6$ | 110.8 |
| T172R/G173Q/L196C/I301C | 3,709 | 556.7 | $1.50 \times 10^5$ | 2.6 |
| T172R/G173Q/L196C/I301C/V116K | 46.26 | 568.6 | $1.23 \times 10^7$ | 210.3 |
| T172R/G173Q/L196C/I301C/V116K/A51L | 27.84 | 873 | $3.14 \times 10^7$ | 536.5 |
| T172R/G173Q/L196C/I301C/V116K/A51Y | 43.59 | 910.6 | $2.09 \times 10^7$ | 357.4 |
| T172R/G173Q/L196C/I301C/V116K/A51V | 86.16 | 693.2 | $8.05 \times 10^6$ | 137.6 |
| T172R/G173Q/L196C/I301C/V116K/A51F | 59.29 | 733.9 | $1.24 \times 10^7$ | 211.8 |
| T172R/G173Q/L196C/I301C/V116K/A51W | 95.64 | 740.7 | $7.74 \times 10^6$ | 132.5 |

Note:
$K_{eff}$ refers to the catalytic efficiency ($k_{cat}/K_M$) of the corresponding enzyme to the substrate BZE.
RCE refers to a ratio of the catalytic efficiency of the mutant enzyme to BZE and that of the wildtype enzyme to BZE.

RCE refers to a ratio of the catalytic efficiency of the mutant enzyme to BZE and that of the wildtype enzyme to BZE.

Embodiment 4: In Vivo Experiments in Animals

Experimental male SD rats (200 g/rat) purchased from Laboratory Animal Center of Zhejiang Academy of Medical Sciences were raised in a constant-temperature and constant-humidity environment. The feeding and experimental application was carried out by following Guide for the Care and Use of Laboratory Animals.

(1) Standard Curves for BA and BZE Blood Samples

Blood was collected from the femoral vein of rats using a blood collection needle and a heparin-treated capillary. Firstly, eight tubes of blood from the same rat, 75 μL in each tube, were added to 100 μL of 250 μM paraxon to inhibit the effect of endogenous metabolizing enzymes on BZE, and frozen at −80° C. After thawing, 19.7 μL of mixed solution containing 0, 4, 10, 20, 40, 60, 100 and 200 μM BA and BE standards, then subjected to vortex for 20 seconds, and then added with 150 μL of acetonitrile and subjected to vortex for 1 minutes, then added with 50 μL of 10% HClO$_4$ and subjected to vortex for 1 minutes, centrifuged at 17,000 rcf for 15 minutes, and then centrifuged again after the supernatant was transferred. 250 μL of supernatant were taken out for HPLC analysis. The sample volume was 100 μL, and the HPLC experimental conditions were the same as those in Embodiment 3. The concentrations of BZE and BA in the final standard samples were 0, 0.2, 0.5, 1, 2, 3, 5 and 10 μM respectively.

(2) High-Activity CocE Mutant Accelerated BZE Metabolism In Vivo

There were 5 rats in each group. Firstly, 0.2 or 1 mg/kg of high-active CocE mutant or normal saline was injected into the tail vein of rats, and 2 mg/kg BZE was injected into the tail vein within 1 minute. After BZE injection, 75 μL of blood samples were taken at the $0^{th}$, $2^{nd}$, $5^{th}$, $10^{th}$, $30^{th}$, $60^{th}$, $90^{th}$ and $120^{th}$ minutes respectively, and 100 μL of 250 μM paraxon were added in each sample, and then frozen at $-80°$ C. After thawing, the samples were subjected to vortex for 20 seconds, then added with 150 μL of acetonitrile and subjected to vortex for 1 minute, then added with 50 μL of 10% $HClO_4$ and subjected to vortex for 1 minute, centrifuged at 17,000 g for 15 minutes, and then centrifuged again after the supernatant was transferred. 250 μL of supernatant were taken out for HPLC analysis. The sample volume was 100 μL. The BA and BZE concentrations in the blood of rats in each group at different time points were calculated according to the blood sample standard curve of the standards, so as to obtain the metabolism of BZE with or without the high-activity CocE mutant.

Figure 3A:
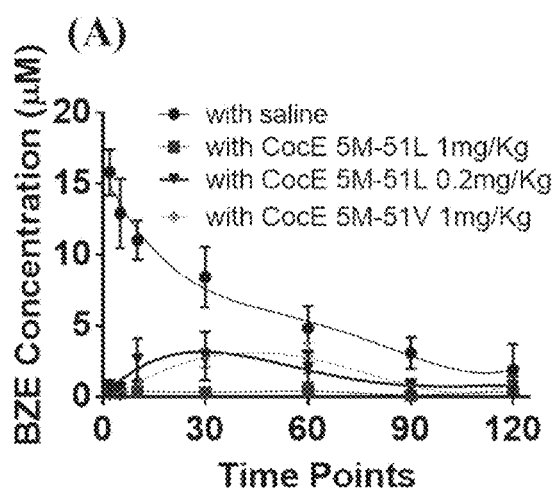
FIGS. 3A and 3B are graphs showing a high-activity CocE mutant accelerating BZE metabolism in rats.
Figure 3B:
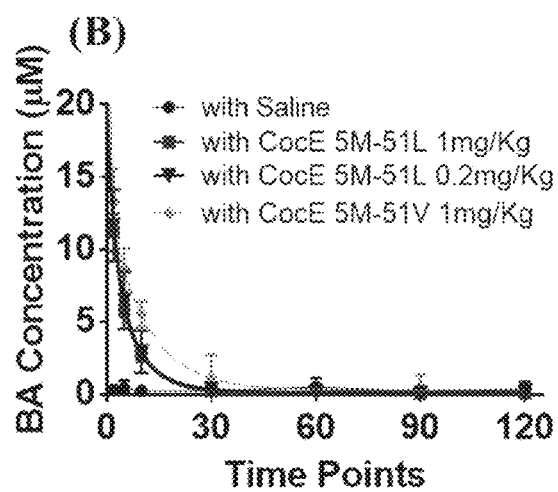

The results were shown in FIGS. 3A and 3B. The results showed that after intravenous injection of 2 mg/kg of BZE in the rats, the BZA concentration in the blood was as high as 15.8 μM and the BA concentration in the blood was less than 0.5 μM at the second minutes. When the high-activity mutant was injected, the BZA concentration in the blood of rats decreased rapidly while the BA concentration in the blood increased rapidly, which indicated that the toxic BZE in the rats was quickly eliminated by the high-activity mutant and metabolized into non-toxic BA.

The invention claimed is:

1. A cocaine esterase mutant obtained by mutating a wildtype cocaine esterase, wherein an amino acid sequence of the wildtype cocaine esterase is shown as SEQ ID NO: 1, and the cocaine esterase mutant is one of the following:
   (1) the SEQ ID NO: 1 having a mutation at a site of the 116th position, wherein the mutation is V116K,
   (2) the SEQ ID NO: 1 having three mutations at sites of the 172nd position, the 173rd position, and the 116th position, wherein the three mutations are: T172R, G173Q, and V116K,
   (3) the SEQ ID NO: 1 having five mutations at sites of the 172nd position, the 173rd position, the 196th position, the 301st position, the 116th position, wherein the five mutations are: T172R, G173Q, L196C, I301C, and V116K,
   (4) the SEQ ID NO: 1 having six mutations at sites of the 172nd position, the 173rd position, the 196th position, the 301st position, the 116th position, and 51st position, wherein the six mutations are: T172R, G173Q, L196C, I301C, V116K, and A51L,
   (5) the SEQ ID NO: 1 having six mutations at sites of the 172nd position, the 173rd position, the 196th position, the 301st position, the 116th position, and 51st position, wherein the six mutations are: T172R, G173Q, L196C, I301C, V116K, and A51Y,
   (6) the SEQ ID NO: 1 having six mutations at sites of the 172nd position, the 173rd position, the 196th position, the 301st position, the 116th position, and 51st position, wherein the six mutations are: T172R, G173Q, L196C, I301C, V116K, and A51V,
   (7) the SEQ ID NO: 1 having six mutations at sites of the 172nd position, the 173rd position, the 196th position, the 301st position, the 116th position, and 51st position, wherein the six mutations are: T172R, G173Q, L196C, I301C, V116K, and A51F, or
   (8) the SEQ ID NO: 1 having six mutations at sites of the 172nd position, the 173rd position, the 196th position, the 301st position, the 116th position, and 51st position, wherein the six mutations are: T172R, G173Q, L196C, I301C, V116K, and A51W.

2. A medicament for treating cocaine intoxication, the medicament comprising the cocaine esterase mutant according to claim 1.

3. A hydrolytic agent for hydrolyzing benzoylecgonine into ecgonine and benzoic acid, the hydrolytic agent comprising the cocaine esterase mutant according to claim 1.

4. An agent for treating cocaine or benzoylecgonine contamination in water or soil, the agent comprising the cocaine esterase mutant according to claim 1.

* * * * *

```
                        SEQUENCE LISTING

Sequence total quantity: 37
SEQ ID NO: 1           moltype = AA  length = 574
FEATURE                Location/Qualifiers
source                 1..574
                       mol_type = protein
                       organism = Rhodococcus sp.
SEQUENCE: 1
MVDGNYSVAS NVMVPMRDGV RLAVDLYRPD ADGPVPVLLV RNPYDKFDVF AWSTQSTNWL   60
EFVRDGYAVV IQDTRGLFAS EGEFVPHVDD EADAEDTLSW ILEQAWCDGN VGMFGVSYLG  120
VTQWQAAVSG VGGLKAIAPS MASADLYRAP WYGPGGALSV EALLGWSALI GRQLITSRSD  180
ARPEDAADFV QLAAICNDVA GAASVTPLAE QPLLGRLIPW VIDQVVDHPD NDESWQSISL  240
FERLGGLATP ALITAGWYDG FVGESLRTFV AVKDNADARL VVGPWSHSNL TGRNADRKFG  300
CAATYPIQEA TTMHKAFFDR HLRGETDALA GVPKVRLFVM GIDEWRDETD WPLPDTAYTP  360
FYLGGSGAAN TSTGGGTLST SISGTESADT YLYDPADPVP SLGGTLLFHN GDNGPADQRP  420
IHDRDDVLCY STEVLTDPVE VTGTVSARLF VSSSAVDTDF TAKLVDVFPD GRAIALCDGI  480
VRMRYRETLV NPTLIEAGEI YEVAIDMLAT SNVFLPGHRI MVQVSSSNFP KYDRNSNTGG  540
VIAREQLEEM CTAVNRIHRG PEHPSHIVLP IIKR                              574

SEQ ID NO: 2           moltype = DNA  length = 28
FEATURE                Location/Qualifiers
source                 1..28
                       mol_type = other DNA
                       organism = synthetic construct
SEQUENCE: 2
ctctcatagg tcgccagctc atcacgtc                                     28

SEQ ID NO: 3           moltype = DNA  length = 28
FEATURE                Location/Qualifiers
source                 1..28
                       mol_type = other DNA
                       organism = synthetic construct
SEQUENCE: 3
gacgtgatga gctggcgacc tatgagag                                     28

SEQ ID NO: 4           moltype = DNA  length = 25
FEATURE                Location/Qualifiers
source                 1..25
                       mol_type = other DNA
                       organism = synthetic construct
SEQUENCE: 4
ctcgcagcaa tttgcaatga cgtcg                                        25

SEQ ID NO: 5           moltype = DNA  length = 25
FEATURE                Location/Qualifiers
source                 1..25
                       mol_type = other DNA
                       organism = synthetic construct
SEQUENCE: 5
cgacgtcatt gcaaattgct gcgag                                        25

SEQ ID NO: 6           moltype = DNA  length = 26
FEATURE                Location/Qualifiers
source                 1..26
                       mol_type = other DNA
                       organism = synthetic construct
SEQUENCE: 6
```
ggaagttcgg ctgcgccgcg acctac                                              26

SEQ ID NO: 7            moltype = DNA   length = 26
FEATURE                 Location/Qualifiers
source                  1..26
                        mol_type = other DNA
                        organism = synthetic construct
SEQUENCE: 7
gtaggtcgcg gcgcagccga acttcc                                              26

SEQ ID NO: 8            moltype = DNA   length = 32
FEATURE                 Location/Qualifiers
source                  1..32
                        mol_type = other DNA
                        organism = synthetic construct
SEQUENCE: 8
atgtgggcat gttcggcttt tcgtacttgg gt                                       32

SEQ ID NO: 9            moltype = DNA   length = 32
FEATURE                 Location/Qualifiers
source                  1..32
                        mol_type = other DNA
                        organism = synthetic construct
SEQUENCE: 9
acccaagtac gaaaagccga acatgcccac at                                       32

SEQ ID NO: 10           moltype = DNA   length = 22
FEATURE                 Location/Qualifiers
source                  1..22
                        mol_type = other DNA
                        organism = synthetic construct
SEQUENCE: 10
gtgttcttgt ggtcgacgca gt                                                  22

SEQ ID NO: 11           moltype = DNA   length = 22
FEATURE                 Location/Qualifiers
source                  1..22
                        mol_type = other DNA
                        organism = synthetic construct
SEQUENCE: 11
actgcgtcga ccacaagaac ac                                                  22

SEQ ID NO: 12           moltype = DNA   length = 30
FEATURE                 Location/Qualifiers
source                  1..30
                        mol_type = other DNA
                        organism = synthetic construct
SEQUENCE: 12
ttcgacgtgt tctactggtc gacgcagtcg                                          30

SEQ ID NO: 13           moltype = DNA   length = 30
FEATURE                 Location/Qualifiers
source                  1..30
                        mol_type = other DNA
                        organism = synthetic construct
SEQUENCE: 13
cgactgcgtc gaccagtaga acacgtcgaa                                          30

SEQ ID NO: 14           moltype = DNA   length = 23
FEATURE                 Location/Qualifiers
source                  1..23
                        mol_type = other DNA
                        organism = synthetic construct
SEQUENCE: 14
gacgtgttcg tttggtcgac gca                                                 23

SEQ ID NO: 15           moltype = DNA   length = 23
FEATURE                 Location/Qualifiers
source                  1..23
                        mol_type = other DNA
                        organism = synthetic construct
SEQUENCE: 15
tgcgtcgacc aaacgaacac gtc                                                 23

SEQ ID NO: 16           moltype = DNA   length = 32
FEATURE                 Location/Qualifiers
source                  1..32
                        mol_type = other DNA
                        organism = synthetic construct

| | | |
|---|---|---|
| SEQUENCE: 16 ccatacgaca agttcgacgt gttcttctgg tc | | 32 |
| SEQ ID NO: 17 FEATURE source  SEQUENCE: 17 | moltype = DNA   length = 32 Location/Qualifiers 1..32 mol_type = other DNA organism = synthetic construct | |
| gaccagaaga acacgtcgaa cttgtcgtat gg | | 32 |
| SEQ ID NO: 18 FEATURE source  SEQUENCE: 18 | moltype = DNA   length = 32 Location/Qualifiers 1..32 mol_type = other DNA organism = synthetic construct | |
| ccatacgaca agttcgacgt gttctggtgg tc | | 32 |
| SEQ ID NO: 19 FEATURE source  SEQUENCE: 19 | moltype = DNA   length = 32 Location/Qualifiers 1..32 mol_type = other DNA organism = synthetic construct | |
| gaccaccaga acacgtcgaa cttgtcgtat gg | | 32 |
| SEQ ID NO: 20 FEATURE source  SEQUENCE: 20 | moltype = DNA   length = 28 Location/Qualifiers 1..28 mol_type = other DNA organism = synthetic construct | |
| ctctcatagg tcgccagctc atcacgtc | | 28 |
| SEQ ID NO: 21 FEATURE source  SEQUENCE: 21 | moltype = DNA   length = 28 Location/Qualifiers 1..28 mol_type = other DNA organism = synthetic construct | |
| gacgtgatga gctggcgacc tatgagag | | 28 |
| SEQ ID NO: 22 FEATURE source  SEQUENCE: 22 | moltype = DNA   length = 25 Location/Qualifiers 1..25 mol_type = other DNA organism = synthetic construct | |
| ctcgcagcaa tttgcaatga cgtcg | | 25 |
| SEQ ID NO: 23 FEATURE source  SEQUENCE: 23 | moltype = DNA   length = 25 Location/Qualifiers 1..25 mol_type = other DNA organism = synthetic construct | |
| cgacgtcatt gcaaattgct gcgag | | 25 |
| SEQ ID NO: 24 FEATURE source  SEQUENCE: 24 | moltype = DNA   length = 26 Location/Qualifiers 1..26 mol_type = other DNA organism = synthetic construct | |
| ggaagttcgg ctgcgccgcg acctac | | 26 |
| SEQ ID NO: 25 FEATURE source  SEQUENCE: 25 | moltype = DNA   length = 26 Location/Qualifiers 1..26 mol_type = other DNA organism = synthetic construct | |
| gtaggtcgcg gcgcagccga acttcc | | 26 |
| SEQ ID NO: 26 FEATURE source | moltype = DNA   length = 32 Location/Qualifiers 1..32 mol_type = other DNA | |

-continued

```
                           organism = synthetic construct
SEQUENCE: 26
atgtgggcat gttcggcttt tcgtacttgg gt                                    32

SEQ ID NO: 27              moltype = DNA   length = 32
FEATURE                    Location/Qualifiers
source                     1..32
                           mol_type = other DNA
                           organism = synthetic construct
SEQUENCE: 27
acccaagtac gaaaagccga acatgcccac at                                    32

SEQ ID NO: 28              moltype = DNA   length = 22
FEATURE                    Location/Qualifiers
source                     1..22
                           mol_type = other DNA
                           organism = synthetic construct
SEQUENCE: 28
gtgttcttgt ggtcgacgca gt                                               22

SEQ ID NO: 29              moltype = DNA   length = 22
FEATURE                    Location/Qualifiers
source                     1..22
                           mol_type = other DNA
                           organism = synthetic construct
SEQUENCE: 29
actgcgtcga ccacaagaac ac                                               22

SEQ ID NO: 30              moltype = DNA   length = 30
FEATURE                    Location/Qualifiers
source                     1..30
                           mol_type = other DNA
                           organism = synthetic construct
SEQUENCE: 30
ttcgacgtgt tctactggtc gacgcagtcg                                       30

SEQ ID NO: 31              moltype = DNA   length = 30
FEATURE                    Location/Qualifiers
source                     1..30
                           mol_type = other DNA
                           organism = synthetic construct
SEQUENCE: 31
cgactgcgtc gaccagtaga acacgtcgaa                                       30

SEQ ID NO: 32              moltype = DNA   length = 23
FEATURE                    Location/Qualifiers
source                     1..23
                           mol_type = other DNA
                           organism = synthetic construct
SEQUENCE: 32
gacgtgttcg tttggtcgac gca                                              23

SEQ ID NO: 33              moltype = DNA   length = 23
FEATURE                    Location/Qualifiers
source                     1..23
                           mol_type = other DNA
                           organism = synthetic construct
SEQUENCE: 33
tgcgtcgacc aaacgaacac gtc                                              23

SEQ ID NO: 34              moltype = DNA   length = 32
FEATURE                    Location/Qualifiers
source                     1..32
                           mol_type = other DNA
                           organism = synthetic construct
SEQUENCE: 34
ccatacgaca agttcgacgt gttcttctgg tc                                    32

SEQ ID NO: 35              moltype = DNA   length = 32
FEATURE                    Location/Qualifiers
source                     1..32
                           mol_type = other DNA
                           organism = synthetic construct
SEQUENCE: 35
gaccagaaga acacgtcgaa cttgtcgtat gg                                    32

SEQ ID NO: 36              moltype = DNA   length = 32
FEATURE                    Location/Qualifiers
source                     1..32
```

| | | |
|---|---|---|
| | mol_type = other DNA<br>organism = synthetic construct | |
| SEQUENCE: 36 | | |
| ccatacgaca agttcgacgt gttctggtgg tc | | 32 |
| | | |
| SEQ ID NO: 37<br>FEATURE<br>source | moltype = DNA  length = 32<br>Location/Qualifiers<br>1..32<br>mol_type = other DNA<br>organism = synthetic construct | |
| SEQUENCE: 37 | | |
| gaccaccaga acacgtcgaa cttgtcgtat gg | | 32 |